(12) United States Patent
Jenkins, Jr.

(10) Patent No.: US 7,712,469 B2
(45) Date of Patent: May 11, 2010

(54) DETECTABLE EARPLUG AND CORD

(75) Inventor: John Allen Jenkins, Jr., San Diego, CA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 1001 days.

(21) Appl. No.: 11/083,762

(22) Filed: Mar. 18, 2005

(65) Prior Publication Data

US 2005/0229938 A1    Oct. 20, 2005

Related U.S. Application Data

(60) Provisional application No. 60/562,360, filed on Apr. 15, 2004.

(51) Int. Cl.
*A61F 11/00* (2006.01)

(52) U.S. Cl. ..................................... 128/864

(58) Field of Classification Search ................. 128/854, 128/845, 864, 865, 866, 867, 868; 181/129, 181/130, 131, 132, 133, 134, 135, 284; D24/106
See application file for complete search history.

(56) References Cited

U.S. PATENT DOCUMENTS

| | | | | |
|---|---|---|---|---|
| 2,804,072 A | * | 8/1957 | Genzer | 128/864 |
| 3,881,570 A | * | 5/1975 | Lewis | 181/135 |
| D242,743 S | * | 12/1976 | Leight | D24/106 |
| D253,723 S | * | 12/1979 | Leight | D24/106 |
| 4,936,411 A | | 6/1990 | Leonard | |
| 5,203,352 A | * | 4/1993 | Gardner, Jr. | 128/864 |
| 5,400,296 A | * | 3/1995 | Cushman et al. | 181/284 |
| 5,573,015 A | * | 11/1996 | Williams | 128/864 |
| 5,727,566 A | | 3/1998 | Leight | |
| 5,806,526 A | * | 9/1998 | Rhoad | 128/864 |
| 5,957,136 A | * | 9/1999 | Magidson et al. | 128/864 |
| 6,129,175 A | * | 10/2000 | Tutor et al. | 181/135 |
| 6,256,396 B1 | * | 7/2001 | Cushman | 181/135 |
| 6,920,956 B1 | * | 7/2005 | Falco | 181/135 |

* cited by examiner

*Primary Examiner*—Patricia M Bianco
*Assistant Examiner*—Camtu T Nguyen
(74) *Attorney, Agent, or Firm*—Leon D. Rosen

(57) ABSTRACT

Earplugs (22, 24) and a combination (20) of a pair earplugs and a cord (26) that joins them, each can be detected by metal and/or magnetic detectors even if the parts of the combination becomes separated and fall into a batch of food, etc. Each earplug includes an earplug core (32) formed of a first elastomer with a multiplicity of metal-mag detectable particles (36) (particles detectable by electrical or magnetic detectors) embedded in the first elastomer, and an earplug covering (32) of a second elastomer (that may be the same as the first one) that is devoid of such particles. The cord includes a cord core (50) formed of a first flexible polymer with metal-mag detectable particles embedded therein, and a cord covering (54) formed of a second polymer that is devoid of such particles. The particles are preferably of iron, which is magnetically detectable but that can mark skin or clothing that it contacts, but which is isolated from the skin and clothing by the earplug and cord coverings. The earplug covering can be molded and then filed with the earplug core. The cord core can be extruded and the covering extruded around the core.

2 Claims, 2 Drawing Sheets

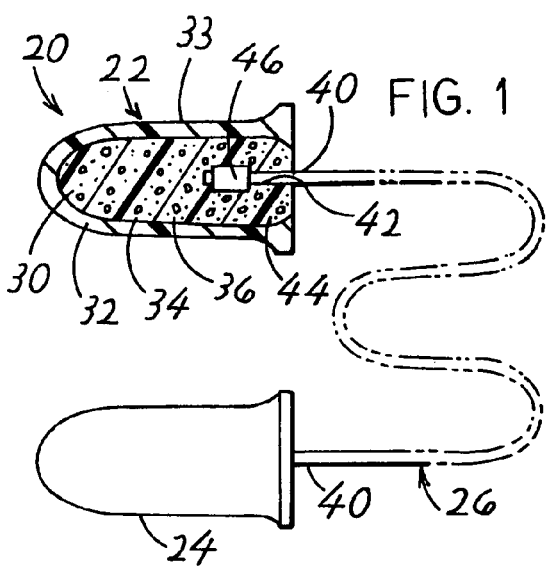
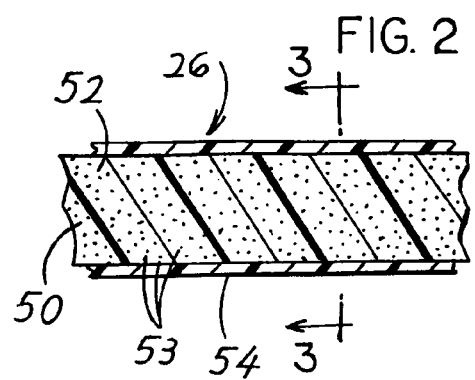
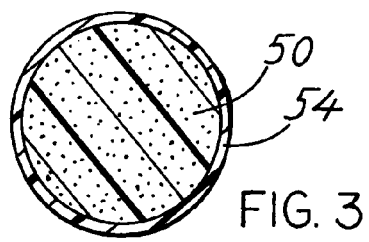
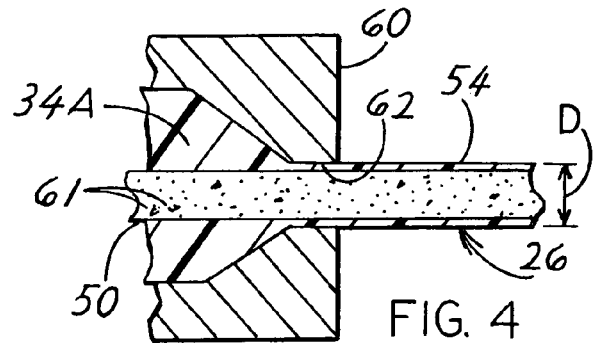
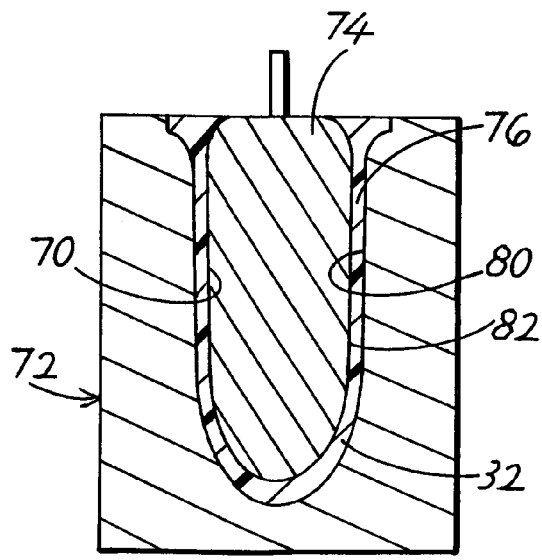
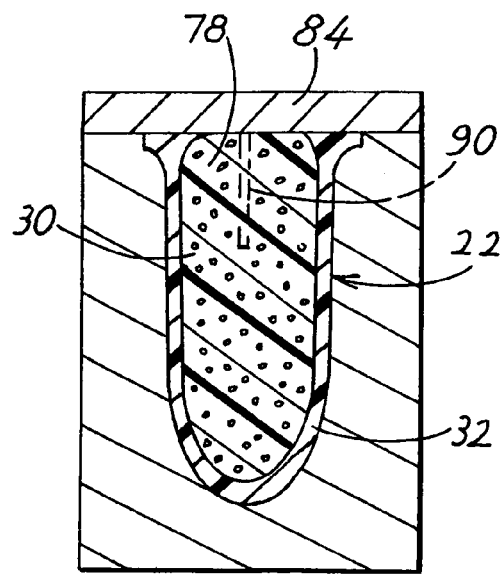

DETECTABLE EARPLUG AND CORD

CROSS-REFERENCE

Applicant claims priority from U.S. provisional patent application Ser. No. 60/562,360 filed Apr. 15, 2004.

BACKGROUND OF THE INVENTION

Earplugs are commonly worn by workers who are subjected to loud noise, to protect their hearing. Occasionally, an earplug may fall from a worker, as when he/she is handling it as to pull it out or push it into the ear canal. In contamination-sensitive processes such as in the preparation of food or medicine, steps are taken to minimize the possibility that an earplug will fall into the material being produced. This often involves tying together a pair of earplugs with a cord. The cord may limit falling of one of the earplugs as where the other earplug is held in the worker's ear or the cord is separately held. In addition, an earplug that falls into a batch of food or medicine must be detected.

Earplugs and cords can be detected by attaching a metal fitting to the earplug or cord for detection by a metal detector. It is usually preferred that the metal be detectable by a magnetic detector, and an iron based alloy is usually preferred because it is of low cost and sensitive to detection by a magnetic detector. Magnetic detectors are often more sensitive than metal detectors. Applicant notes that certain ceramics (which are as hard as hard metals) are magnetically detectable and are the equivalent of metal for the purposes of the invention. Both the earplug and any cord that connects them should be separately detectable because an earplug may become detached from a cord. U.S. Pat. No. 4,936,411 describes the placement of a metal ball of about 2 millimeters diameter (and 6 cubic millimeters volume) in a deep passage in the rear of an earplug and the placement of a metal ring or crimp barrel of about 2 millimeters diameter and 8 millimeters length (volume of about 2 cubic millimeters) around a cord, to detect either one by magnetic, electrical or x-ray detectors. U.S. Pat. No. 5,727,566 describes a metal ring of about 0.2 inch diameter (5 millimeters diameter and a volume of about 5 cubic millimeters) attached to an earplug for detection.

Although the presence of a metal ball or ring greatly helps detect an earplug or cord, there is still a possibility that the earplug or cord will go undetected. If undetected in material being processed, a metal ball or ring of about 2 millimeters diameter may be even more disastrous than a solely polymer earplug or cord. Such metal piece may do more damage to a person eating the metal piece or to machinery that processes the material, than a solely polymer earplug or cord.

It would be desirable if a corded earplug pair comprising a pair of earplugs and a cord with opposite ends attached to the earplugs, were constructed so that all components of the combination could be detected by a metal and/or magnetic detector. It would be especially desirable if the earplugs and/or cord were separately detectable by metal and magnetic detectors, without the earplugs or cord containing a metal piece of appreciable diameter or volume (more than 0.1 cubic millimeter).

SUMMARY OF THE INVENTION

In accordance with one embodiment of the invention, applicant provides earplugs and cords and a combination of them and manufacturing methods therefor, which enables their detection by metal and/or magnetic detectors without including large hard pieces in them. The earplugs and cord each have a portion formed of a flexible polymer with small particles therein of metal-mag detectable material; that is, of material which is detectable by metal and/or magnetic detectors. There are sufficient particles in the polymer, such as at least 0.2 cubic millimeters of particles, so the particles can be readily detected. The particles are small enough that numerous particles can be readily mixed into a polymer that is shaped as an earplug or cord or that forms a core of an earplug or cord.

All metals are detectable by metal detectors, but few metals are detectable by magnetic detectors. An iron alloy is detectable by both and is of low cost. Disposable earplugs sell for only a few cents (US) each, so a low cost particle material is desirable. Thus, applicant prefers to use particles of an iron alloy in the earplugs and cord. However, for most iron alloys, if a particle rubs against clothing or the skin, the particle leaves a red mark. To prevent this, applicant forms the earplugs and cord each with a core containing iron alloy particles, and each with a covering that is devoid of the particles.

The earplug contains an earplug core of an polymer (preferably elastomeric) in which a plurality of metal-mag particles is embedded, preferably of iron alloy. The earplug core is covered over most of its outside area with an elastomeric covering that is devoid of such particles. The cord is formed of a flexible polymer that usually is not elastomeric. The cord includes a cord core of flexible polymer that contains embedded metal-mag particles, and a covering of a flexible polymer that is devoid of such particles.

The earplugs can be formed by molding a particle-free elastomeric polymer in a mold, with a molding core taking up most of the volume of the cavity. The molding core is removed to leave a covering in the mold. Then, a flowable polymer containing the metal-mag particles is flowed into the volume in the covering.

The core can be formed by first extruding a cord core of flexible material containing metal-mag particles. Then the cord core is passed though another extrusion die while the cord covering material containing a flexible polymer devoid of the particles, is extruded around the cord core.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side view of a combination of two earplugs and a cord that connects them, with one earplug shown in section, the combination being constructed in accordance with one embodiment of the invention.

FIG. 2 is a partial sectional view of the cord of the combination of FIG. 1

FIG. 3 is a sectional view taken on line 3-3 of FIG. 2.

FIG. 4 is a partial sectional view showing a method for constructing the cord of FIG. 2.

FIG. 5 is a sectional view of a mold with an earplug covering molded between the mold cavity and an a mold armature, and showing one step in the molding of the earplug of FIG. 1.

FIG. 6 is a sectional view similar to that of FIG. 5, but with the armature removed and an earplug core molded within the covering.

DESCRIPTION OF THE PREFERRED EMBODIMENTS

Figure 7:
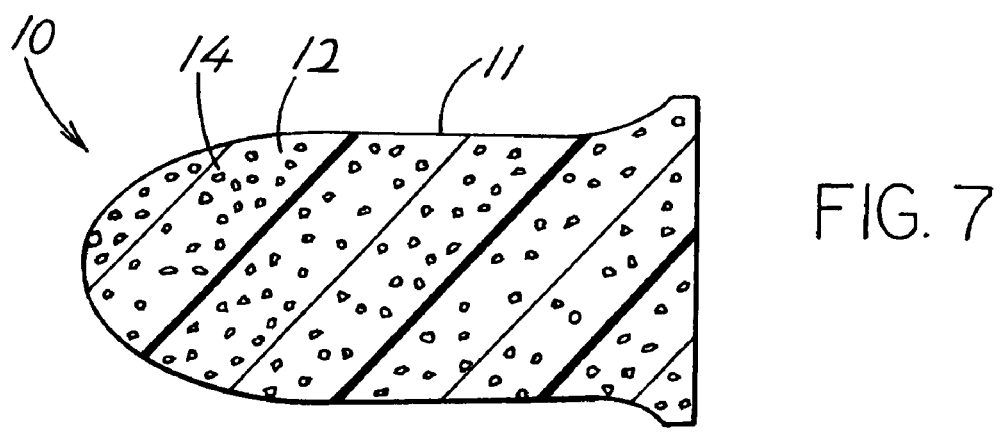
FIG. 7 is a sectional view of an earplug constructed in accordance with another embodiment of the invention.
Figure 8:
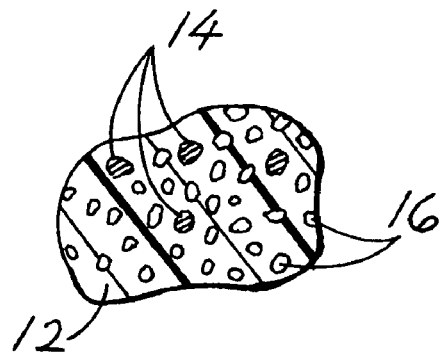
FIG. 8 is an enlarged view of a portion of FIG. 7.

FIGS. 7 and 8 illustrate an earplug 10 that has a molded earplug body 11 of an elastomeric polymer 12, and that also has a multiplicity (at least three) of particles 14 in the polymer. The particular polymer 12 is a foam and the drawings show gas bubbles 16 interspersed with the particles 14. The particles are formed of a material that is detectable by a metal detector and/or a magnetic material detector, and such material that is detectable by one or both detectors is hereinafter referred to as a "metal-mag" material. An iron alloy is a metal-mag material that is detectable by both a metal detector and a magnetic material detector. Magnetic material detectors are generally more sensitive than metal detectors and are preferred. All metals, such as aluminum, copper and silver are detectable by a metal detector. Applicant notes that elastomeric materials can be defined as materials have a Young's modulus of elasticity of 50,000 psi or less.

Instead of using a single easily detected object in the polymer of the earplug of FIGS. 7 and 8, applicant uses a large number of substantially microscopic particles, which may have been tumbled to avoid sharp edges, to avoid a particle scratching a person's skin, and to avoid or minimize harm to a person or to machinery that processes food or other material into which the earplug may fall. A particle having a diameter and length each no more than 0.02 inch (0.5 mm) is substantially microscopic. A particle of 0.02 inch diameter and 0.02 inch length has a volume of $8 \times 10^{-6}$ inch (0.1 cubic millimeter). Actually, applicant prefers to use particles each having a volume less than 0.01 cubic millimeter for the earplug of FIGS. 7 and 8. However, applicant prefers to use a total volume of such particles of at least 0.2 cubic millimeter and preferably at least 0.5 cubic millimeter so it can be readily detected. The particles are embedded in the polymer of the earplug body, so the particles are surrounded (and primarily in contact) with polymer material at most of each particle outside surface.

When the particles are made of iron, the particles produce a red mark on any object they rub against, such as a worker's skin or clothing. This is unacceptable. Also, if the particles are to come in direct contact with a worker's skin, then the particles must be of very small size and preferably be tumbled to remove sharp edges. Thus, while the earplug of FIGS. 7 and 8 can be useful, its cost may be raised because of a construction required to assure that the particles (e.g. of a magnetic stainless steel or silver) do not mark or scratch the wearer. Applicant notes that some earplugs have a hollow body and a stiffer polymer core that helps push the body into the ear canal, and either can have such metal-mag particles.

FIG. 1 illustrates a combination 20 of two identical earplugs 22, 24 and a cord 26 that connects them, all constructed in accordance with a preferred embodiment of the invention. In FIG. 1 each earplug such as 22 includes an earplug core 30 and a sheath or earplug covering 32 that covers the earplug core. A front portion 33 of the earplug has an outside diameter such as 12 mm. The earplug core is slightly smaller but otherwise of the same construction as the earplug of FIG. 7, although it can include larger metal-mag particles of a non-stainless iron alloy. The earplug 22 of FIG. 1 includes a polymer (preferably elastomeric) 34 and a plurality of small particles 36 of metal-mag detectable material such as iron. The covering 32 is formed of a polymer (that is also preferably elastomeric) and that is devoid of metal or other hard particles. Flexible polymers generally have a Young's modulus of less than 1,000,000 psi, while metals have a much higher Young's modulus (e.g. iron has a Young's modulus of 30,000,000 psi). The polymer of the earplug core 30 and of the earplug covering 32 are preferably of the same elastomeric material and are bonded together as by molding one against the other.

The particles 36 in the earplug core may be larger than those in the earplug of FIG. 7 because the particles 36 do not directly contact a person's skin or clothing. However, they must be small enough to minimize harm to people or machinery if they drop into a batch of material, and they should be flowable with the polymer into which they are embedded. Applicant uses more than ten particles in each earplug core and in each cord-core, and preferably uses more than one hundred particles in each. The total volume of particles is at least 0.2 cubic millimeter and preferably at least 0.5 cubic mm in each part to enable its detection by a metal detector and/or magnetic detector.

FIG. 1 shows the cord 26 having ends 40 that each lies in a passage 42 in the rear portion 44 of an earplug core. Each cord end has an enlargement 46 of polymer but the cord can be fixed in the earplug core in other ways as by adhesive. FIG. 2 shows that the cord 26 includes a cord-core or string 50 of a flexible polymer material 52 that has been impregnated with metal-mag particles 53 such as iron, and a cord-covering 54 of a flexible polymer material that is devoid of metal-mag particles. The polymer materials of the cord-core and covering are preferably the same.

Figure 9:
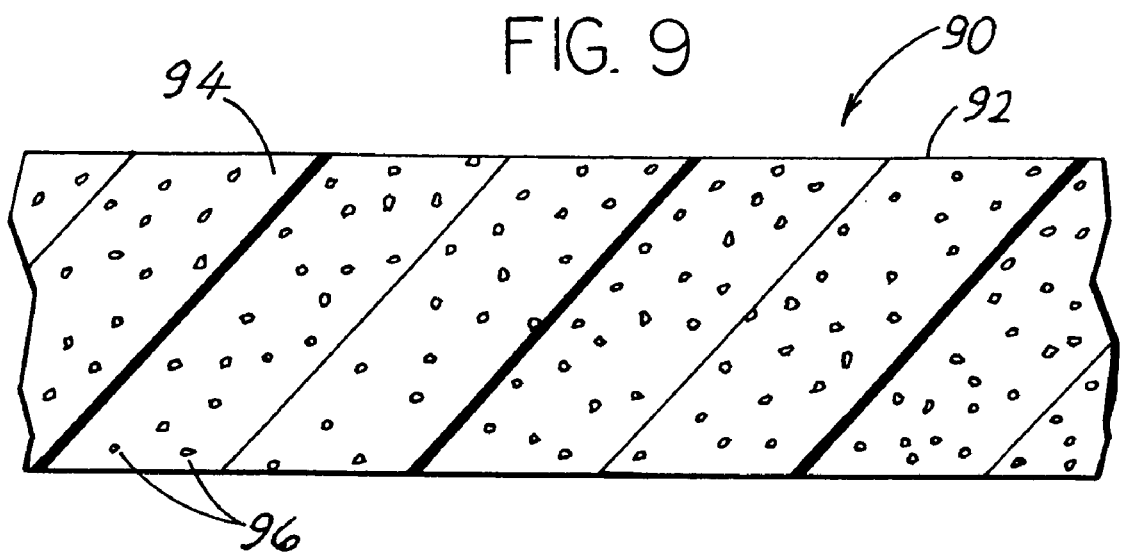
FIG. 9 is a partial enlarged sectional view of a cord of another embodiment of the invention.

FIG. 4 shows one method for forming the cord 26 of FIG. 2. The cord-core or string 50 has been extruded before it reaches a covering extrusion head 60 and preferably was extruded of a flexible polymer with embedded metal-mag particles 61 such as iron. The covering extrusion head 60 has an opening 62 that is of slightly larger diameter than the core to extrude the covering 54 around the core. Where there is a thin covering, the cord-core tends to center itself within the covering extrusion head opening 62. The finished core may be cut into pieces each of a length of about 2 feet (0.6 meter) to enable its use to tie together a pair of earplugs. Another way to produce a cord-covering is to spray a polymer coating around the particle-containing cord core. The cord may have a diameter D of 1.1 millimeter with a cord-covering of 0.1 mm thickness; the cord-covering should be thick enough to prevent any particles from projecting though the covering despite wear. The cord can be of a construction similar to the earplug of FIGS. 7 and 8. FIG. 9 shows such a cord 90 which includes a string 92 solely of a polymer 94 and metal-mag particles 96 embedded in the polymer, with the particles preferably of a corrosion-resistant material such as stainless steel.

FIGS. 5 and 6 show one method for producing the earplugs of FIG. 1. The earplug covering 32 (FIG. 5) is formed first by flowing a polymer (preferably elastomeric) that is devoid of metal particles, in a cavity 70 of a mold 72. An armature 74 is also placed in the mold, to leave a thin (e.g. 1 mm) covering cavity 76 between the mold inner walls 80 and the armature outer walls 82. After the covering 32 has at least partially solidified, the armature 74 is removed. As indicated in FIG. 6, a mixture 78 of a polymer and iron alloy particles that is to form the earplug core, is flowed into the shell formed by the covering 32 and allowed to solidify to form the earplug core 30. The mold may be closed by a cover 84 after one or both steps of flowing material into it, especially where the earplug covering and core are each of foamed slow recovery material. The cover may have a post indicated at 90 to facilitate cord anchoring in the earplug. One disadvantage of the above method is that the molding process takes additional steps so the earplug costs more to manufacture. It is also possible to spray a coating around the earplug core, but the covering should be thick enough (and the particles in the earplug core small and dull enough) that the particles do not form bulges in the covering that can be felt or that will cut though the covering.

Thus, the invention provides earplugs and a cord that can tie together a pair of earplugs, wherein the earplugs and cord are of moderate cost and each can be detectable by a magnetic detector and/or a metal detector. Instead of providing one piece of metal-mag material, applicant provides a multiplicity (at least three) of particles (preferably over 10 and more preferably at least 100) of such material in each earplug core and in the cord core. In one earplug construction, the earplug includes an earplug core containing an elastomeric polymer and metal-mag particles in the polymer, and the earplug also includes a covering of an elastomeric material that is devoid of metal-mag particles. The particles are small enough that they avoid or minimize harm to people and machinery and can readily flow with the flowable polymer during molding. The covering is thick enough, compared to the particle size and sharpness, that particles do not bulge out or cut the covering. The total volume of the metal-mag particles is at least 0.2 cubic millimeters and preferably at least 0.5 cubic millimeter so the metal-mag material is readily detectable. The cord includes a cord-core of flexible polymer with metal-mag particles embedded therein, and a covering of flexible polymer that is devoid of metal-mag particles. The earplugs can be molded by molding the covering first and then flowing the earplug core into the covering. The cord can be formed by first extruding the polymer-particle cord and then passing it though an extrusion head while covering material is extruded around the cord-core. In both cases, of the core and covering one is molded to the other (it solidifies while in contact with the other) to bond them together without adhesive.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug comprising:
   an earplug core formed of a polymer material and a multiplicity of metal-mag detectable particles in the earplug core;
   an earplug-covering of a polymer material that surrounds a majority of said earplug core, said earplug-covering being devoid of metal-mag detectable particles;
   wherein said metal-mag detectable particles are of metal, each has a volume less than $8\times10^{-6}$ cubic inch (0.1 cubic millimeter).

2. An earplug assembly comprising:
   a first earplug core formed of a polymer material and a multiplicity of metal-mag detectable particles in the earplug core;
   a second earplug core formed of the same construction as said first earplug core;
   an earplug-covering of a polymer material that surrounds a majority of said first earplug core and said second earplug core, said earplug-covering being devoid of metal-mag detectable particles;
   a cord that joins said first earplug core and said second earplug core, said cord having opposite core end portions, with one cord end portion lying in a passage in a rear portion of said first earplug core and the other cord end portion lying in a passage in a rear portion of said second earplug core;
   wherein said cord includes an elongate cord-core of flexible polymer material, and a plurality of particles of metal-mag detectable particles embedded in said cord-core;
   said cord-core also includes a cord-covering of flexible polymer material that surrounds said cord-core, said cord-covering being devoid of particles of metal-mag detectable material.

* * * * *